United States Patent [19]

Isono et al.

[11] Patent Number: 5,478,585
[45] Date of Patent: Dec. 26, 1995

[54] PROCESS FOR PRODUCING LIPOPROTEIN-CONTAINING SUBSTANCE HAVING REDUCED LIPID CONTENT

[75] Inventors: Yoshikazu Isono, Otsu; Michiyo Fukumoto, Osaka; Hitoshi Hariu, Kyoto; Masakazu Takahashi, Kakogawa, all of Japan

[73] Assignees: Sumitomo Seika Chemicals Co., Ltd., Kyogo; Otsuka Foods Co., Ltd., Osaka; Mitsubishi Corporation, Tokyo, all of Japan

[21] Appl. No.: 264,749

[22] Filed: Jun. 23, 1994

Related U.S. Application Data

[63] Continuation of Ser. No. 935,182, Aug. 26, 1992, abandoned.

[30] Foreign Application Priority Data

Sep. 3, 1991 [JP] Japan ..................... 3-222710
Nov. 6, 1991 [JP] Japan ..................... 3-289837

[51] Int. Cl.$^6$ ..................................... A23L 1/32
[52] U.S. Cl. ................ 426/417; 426/32; 426/35; 426/56; 426/422; 426/614
[58] Field of Search ................. 426/32, 34, 35, 426/55, 56, 614, 417, 422, 429, 330.1

[56] References Cited

U.S. PATENT DOCUMENTS

| | | | |
|---|---|---|---|
| 3,563,765 | 2/1971 | Melnick | 426/614 |
| 4,103,040 | 7/1978 | Fioriti et al. | 426/614 |
| 4,313,962 | 2/1982 | Kim et al. | 426/42 |
| 4,333,959 | 6/1982 | Bracco et al. | 426/614 |
| 4,925,790 | 5/1990 | Blanch et al. | 435/52 |
| 5,037,661 | 8/1991 | Merchant et al. | 426/47 |
| 5,061,505 | 10/1991 | Cully et al. | 426/614 |
| 5,091,203 | 2/1992 | Conte et al. | 426/614 |
| 5,116,628 | 5/1992 | Ogasahara et al. | 426/614 |
| 5,128,162 | 7/1992 | Wrezel et al. | 426/417 |

FOREIGN PATENT DOCUMENTS

| | | | |
|---|---|---|---|
| 1130988 | 9/1982 | Canada | 426/429 |
| 0416561A2 | 3/1991 | European Pat. Off. | |
| 0426425A1 | 5/1991 | European Pat. Off. | |
| 0493045A1 | 7/1992 | European Pat. Off. | |

OTHER PUBLICATIONS

Patent Abstract of Japan, JP-A-41 35 456, Tsuji Seiyu KK.
JP-A-1 106 815, Taiyo Kagaku KK, Abstract.

*Primary Examiner*—Donald E. Czaja
*Assistant Examiner*—Lien Tran
*Attorney, Agent, or Firm*—Jones, Tullar & Cooper

[57] ABSTRACT

There is disclosed a process for producing a lipoprotein-containing substance having a reduced lipid content. The lipid content is reduced by treating a lipoprotein-containing substance with at least one enzyme selected from the group consisting of proteolytic enzymes and lipolytic enzymes and then bringing the substance into contact with a sub- or supercritical fluid to extract a lipid from the substance. The lipid extracted from the substance is separated from the fluid which may be used again in the extraction step. Also disclosed is a food whose raw material is a lipoprotein-containing substance having a reduced lipid content obtained by the above process.

19 Claims, No Drawings

PROCESS FOR PRODUCING LIPOPROTEIN-CONTAINING SUBSTANCE HAVING REDUCED LIPID CONTENT

This is a continuation of application Ser. No. 07/935,182 filed on Aug. 26, 1992 now abandoned.

FIELD OF THE INVENTION

The present invention relates to a process for producing a lipoprotein-containing substance having a reduced lipid content and a food containing the substance thus produced.

BACKGROUND OF THE INVENTION

Lipoproteins are one of the conjugated proteins occurring widely in nature and having a structure in which at least one protein and some lipids are conjugated with each other.

Typical examples of the food materials which have been widely used are milk and egg yolk. For example, most of the proteins and lipids in egg yolk are present in the form of a lipoprotein.

The proteins and lipids, both of which constitute a lipoprotein, are indispensable nutrients to humankind. There is, however, a great demand for food having a low lipid content, based on a tendency to intake an excess of lipids, and people have an increasing consciousness that the intake of particular lipid ingredients such as cholesterol should be controlled.

In particular, egg yolk is a kind of complete nutritious food because not only does it have a good taste and a high nutritive value but also it is rich both in various vitamins and iron content. Also, the functions of egg yolk, such as emulsifiability and thermocoagulability, have been utilized in various forms in processed food. However, because egg yolk contains some lipids, particularly cholesterol, at a high concentration, the intake of egg yolk is often controlled not only to treat patients with hyperlipidemia but also to keep a body in good health for normal healthy people. It is, therefore, requested to reduce the lipid content, particularly cholesterol content, in egg yolk without deteriorating its taste and functions.

On the other hand, much attention is now given to blood plasma of slaughtered animals which has not yet been utilized as a food material but would become a useful protein material in the future. Of course, blood plasma of slaughtered animals also contains a great amount of lipoproteins and is is well known that they are associated with the control of lipid transport and the control of intracellular lipid metabolism. The lipids contained in the lipoproteins is the primary causative substance for development of a peculiar odor. Therefore, the blood plasma of slaughtered animals cannot be expected to find applications as a food material until the lipid content therein is reduced.

A general process is known for removing lipids from lipoprotein-containing substances, in which extraction is conducted with an organic solvent such as ethanol, methanol and chloroform, or a mixture thereof. This process is only used as an analytical technique and no attempt has been made to utilize it on an industrial scale.

In addition, as means for removing lipids from egg yolk which is a typical example of the lipoprotein-containing substances, there have been proposed extraction with dimethylether (JP-B 60-9770) and extraction with supercritical carbon dioxide (JP-A 59-135847, 59-140299 and 3-98541), both of which are removal techniques only applied to egg yolk in a dry state. For the purpose of removing lipids, particularly cholesterol, from liquid egg yolk, there have been proposed a few methods utilizing the mixing of egg yolk with edible oil (U.S. Pat Nos. 3,717,474 and 4,333,959, and GB-2238456). Moreover, a process for removal by extraction of cholesterol from liquid egg yolk which is brought into contact with supercritical carbon dioxide is known from U.S. Pat. Nos. 5,116,628 and 5,238,694.

In the case of a process using an organic solvent, many problems will occur, such as a change in emulsifiability and thermocoagulability, caused by the denaturation of proteins; deterioration of flavor and feel of eating; and residual solvent.

As described above, lipoproteins comprise at least one protein and some lipids ingredients conjugated therewith, and they take a stable structure in water; therefore, any technique which uses a raw material in the dry state has disadvantages in that the protein is denatured and the lipid ingredients are oxidized in the step of heating the raw material. Moreover, the structure of the lipoproteins is broken by removal of water, and therefore, functional characteristics, such as emulsifiability, which are inherent to lipoprotein-containing substances, are deteriorated. Further, the drying step requires a great amount of heat energy, which also makes this technique unfavorable from the economical point of view.

In the process for removing cholesterol by mixing liquid egg yolk with edible oil, much force is required for stirring and shearing, and it is necessary to use a great amount of edible oil as an extraction agent. For this reason, such a process finds no industrial application. Moreover, the lipids contained in the lipoprotein-containing substance may be replaced by the edible oil used as an extraction agent in the step of extraction, thereby making it substantially impossible to reduce the lipid content. Further, much force applied for stirring and shearing, as well as heat generated thereby, may deteriorate the functional characteristics of the lipoprotein-containing substance, similarly to the case of a technique using a raw material in a dry state. Thus, there has been much difficulty so far in the removal of lipids from a lipoprotein-containing substance usually in a liquid state without causing many problems as described above, i.e., without making any change in the properties of the substance and causing any deterioration of its functional characteristics.

A process have been found for removing cholesterol from liquid egg yolk under mild conditions, by utilizing the characteristics of a supercritical fluid and by employing a wetted wall column system in bringing the liquid egg yolk into contact with the supercritical fluid. However, this process requires much time for removal of cholesterol by extraction because lipoproteins have a stable structure as described above, and it cannot yet be said that this process is satisfactory for practical use.

OBJECTS OF THE INVENTION

Under these circumstances, the present invention provides a process for removing lipids from lipoprotein-containing substances without causing the above problems, which is, therefore, favorable from the economical point of view. As a result, it has been found that extraction with a sub- or supercritical fluid after treatment with proteolytic enzymes and/or lipolytic enzymes is useful for reducing the lipid content in lipoprotein-containing substances.

An object of the present invention is to provide a process for producing a lipoprotein-containing substance having a reduced lipid content.

Another object of the present invention is to provide a food containing the substance thus produced.

These objects as well as other objects and advantages of the present invention will become apparent to those skilled in the art from the following description.

SUMMARY OF THE INVENTION

According to the present invention, there is provided a process for producing a lipoprotein-containing substance having a reduced lipid content, which comprises the steps of treating a lipoprotein-containing substance with at least one enzyme selected from the group consisting of proteolytic enzymes and lipolytic enzymes bringing the substance in contact with a sub- or supercritical fluid to extract a lipid therefrom; and separating the extracted lipid from the fluid. The present invention also provides a food whose raw material is a lipoprotein-containing substance having a reduced lipid content produced by the above process.

DETAILED DESCRIPTION OF THE INVENTION

As used herein, lipids to be removed from lipoproteins by the process of the present invention refer mainly to monoglycerides, diglycerides, triglycerides, fatty acids, cholesterol, and phospholipids.

The process of the present invention can be applied to any substance so long as this substance contains lipoproteins. Typical examples of the lipoprotein-containing substances are egg yolk obtained by cracking eggs (including liquid egg yolk), whole egg (including liquid whole egg), treated egg yolk and treated whole egg, to which sugars, salts and the like are added for the purpose of storage and modification, as well as blood plasma of slaughtered animals and milk.

In general, proteolytic enzymes are classified into various enzymes by their sources or activities, i.e., those derived from possible sources such as plants, microorganisms and animals, or those having endopeptidase or exopeptidase activity. The protoclytic enzymes to be used in the present invention are not particularly limited and may be those of any kind. Typical examples of the proteolytic enzymes are Protease A, Protease P, Protease N, Protease S, Newlase F, Papain W-40, Bromelain, Protease M (all manufactured by Amano Seiyaku Co., Ltd.), Ceremix, Alcalase, Neutrase (all manufactured by Novo-Nordisk A/S), Pantidase NP2, Protease YD-SS, Aroase AP-10 (all manufactured by Yakuruto Honsha Co., Ltd.), Sumizyme AP, Sumizyme RP, Sumizyme LP (all manufactured by Shin Nihon Kagaku Kogyo Co., Ltd.), Actinase AS (manufactured by Kaken Pharmaceutical Co., Ltd.), Protin-P, Protin-A (both manufactured by Daiwa Kasei Co., Ltd.) and the like. These enzymes may be used solely or in combination.

The amount of proteolytic enzymes to be used is appropriately determined depending mainly upon the kind and reaction conditions of the respective proteolytic enzymes. Although the amount of proteolytic enzymes to be used is not particularly limited so long as the degree of solubilization in 0.22M trichloroacetic acid (TCA) of proteins in the treated substance ranges from 1.5% to 80%, preferably from 1.5% to 30%, it is preferred to select in the range of about 0.01% to 10% by weight based on the total weight of proteins in the treated substance. When the degree of protein solubilization is lower than 1.5%, the removal of lipids cannot be attained with high efficiency. To the contrary, when the degree of solubilization is higher than 80%, although the objects of the present invention may be attained, there occurs a deterioration of physical properties and qualities of the raw material, which is not practical. The conditions of enzyme reaction are not particularly limited and may be those usually used for each of the above enzymes. In the usual cases, suitable conditions are selected for the purpose of avoiding the thermal denaturation of proteins in the raw material, i.e., a temperature of not higher than 65° C., preferably from about 30° to 60° C., and a reaction time of from about 0.5 to 48 hours, preferably about 0.5 to 10 hours.

The lipolytic enzymes as used herein refer to lipases, lipoprotein lipases and phospholipases, all of which may be derived from any possible source, and more particularly, to lipases, lipoprotein lipases, phospholipase $A_1$, phospholipase $A_2$, phospholipase C and phospholipase D. It is preferred to select from these enzymes suitable lipolytic enzymes for lipid decomposition of lipoproteins in the raw material. Examples of the commercially available lipolytic enzymes are Lipase F, Lipase M, Lipoprotein Lipase, Lipase A, Lipase AY (all manufactured by Amano Seiyaku Co., Ltd.), Porcine Pancreas Lipase (manufactured by Sigma Chemical Company), Lecitase, Palatase (both manufactured by Novo-Nordisk A/S), Lipase "Saiken" (manufactured by Yakuruto Honsha Co., Ltd.), Talipase (manufactured by Tanabe Seiyaku Co., Ltd.) and Lipoprotein Lipase (manufactured by Toyobo Co., Ltd.).

The action of lipolytic enzymes may be such that the decomposition ratio of triglycerides or phospholipids in the treated substance is in the range of from 1% to 80%, preferably from 5% to 50%. If the decomposition ratio is lower than 1%, the efficiency of lipid removal becomes poor. The cases where it is higher than 80% are also not practical, because of a change in the physical properties, such as an increase in the viscosity of the treated substance. Similarly to the case of proteolytic enzymes, the amount and reaction conditions of lipolytic enzymes to be used are not particularly limited so long as the desired decomposition ratio can be obtained. In the process of the present invention, so long as the desired decomposition ratio can be obtained, commercially available immobilized enzymes (e.g., Lipozyme 3A manufactured by Novo-Nordisk A/S) may be used, or the above proteolytic enzymes or lipolytic enzymes may be immobilized on an appropriate support according to a conventional process (e.g., Agric. Biol. Chem., 44,413 (1980); Biotechnol. Bioeng., 14, 1031 (1972); and Anal. Biochem., 55, 282 (1973)) for use as an immobilized enzyme.

In general, lipoproteins have a structure in which a core portion composed of triglycerides and cholesterol esters is covered with a layer composed of phospholipids and cholesterol in free form, and to the surface thereof several kinds of proteins are attached. Most of the proteins have, when they are allowed to form an α-helix, one face consisting almost only of polar amino acid residues and the other face consisting almost only of nonpolar amino acid residues. This amphipathic feature makes it possible to mediate between water and oil, both of which are not compatible with each other, in such a manner that the protein portion of the lipoprotein directs its nonpolar face to neutral lipids and its polar face to the polar portion of the phospholipid or to water phase.

It is, therefore, believed that the proteolytic enzyme used in the present invention partially breaks the coat structure of the lipoprotein, while the lipolytic enzyme causes a slight change in its structure by decomposition of the triglycerides present inside as well as the phospholipids covering them, resulting in an unbalanced polarity of the lipoprotein, whereby the removal of lipids by extraction can readily be made without deteriorating the functional characteristics of the lipoprotein.

Although each of the proteolytic enzymes and lipolytic enzymes may be solely used, it is desired that the kind and reaction conditions of enzymes suitable for the raw material to be treated therewith are determined by an experiment, because a combination of both enzymes may provide an increase in the efficiency of lipid removal.

The sub- or supercritical fluid is defined as a fluid in a state near or above its critical point. For example, the critical temperature and pressure for some fluids are as follows: 9° C. and 50 atm. for ethylene; 31° C. and 73 atm. for carbon dioxide; 37° C. and 71 atm. for nitrous oxide; and 97° C. and 42 atm. for propane. In the process of the present invention, the removal of lipids by extraction is conducted with such a fluid in a state near or above its critical point. The sub- or supercritical fluid has a density near that of liquids and a large diffusion coefficient near that of gaseous materials, and because of these characteristics, rapid and large-scale extraction of various compounds can be attained with high efficiency. Also, a slight change in the pressure and temperature can make it easy to separate the extracts from the fluid.

The fluid to be used in the present invention may be of any kind, if it is in a sub- or supercritical state as described above. Most preferred is carbon dioxide because of its solubility for lipids, safety, bacteriostatic or bactericidal action, economical feature, and possibility of conducting extraction at relatively low temperatures.

For the purpose of increasing the efficiency of lipid removal by extraction or attaining the selective removal by extraction of the particular lipid ingredients, it is also possible to mix a co-solvent with the sub- or supercritical fluid. Examples of the co-solvents to be used for the purpose of increasing the efficiency of lipid removal by extraction are ethanol, methanol, acetone and hexane. The kind and mixing ratio of co-solvents in the sub- or supercritical fluid are not particularly limited. For example, in cases where a substance obtained by the process of the present invention is a food material, it is believed that ethanol is most preferred because of its high safety.

Examples of the co-solvent to be used for the purpose of attaining the selective removal of particular lipid ingredients such as cholesterol and fatty acids are oils such as vegetable oils and animal oils. Among these oils, it is particularly preferred to use palm kernel oil, coconut oil, or medium-chain fatty acid triglycerides prepared therefrom. These oils have a high solubility in the sub- or supercritical fluid, which makes possible the efficient removal by extraction of the particular lipid ingredients. Further, it is also possible to attain the selective removal by extraction of only the particular lipid ingredients, while controlling freely the total lipid content in the lipoprotein-containing substance used as the raw material. Here it should be noted that the co-solvent to be used for this purpose contains few amounts of, preferably no amount of, the particular lipid ingredients to be selectively removed. The use of an oil as the co-solvent may be either by mixing it with a sub- or supercritical fluid, or by adding it to the lipoprotein-containing substance which has been treated with enzymes such as proteolytic enzymes and/or lipolytic enzymes, followed by extraction with a sub- or supercritical fluid. The kind and mixing ratio of oils to be used herein are not particularly limited but should be appropriately determined depending upon the kind of the raw material, the kind of the particular lipid ingredients to be selectively removed and the like.

The purpose of the extraction step of the present invention can be attained by using a sub- or supercritical fluid at a pressure of from 50 to 500 kg/cm$^2$, preferably from 100 to 350 kg/cm$^2$, and a temperature of from 25° to 80° C., preferably from 30° to 60° C. At pressures lower than 50 kg/cm$^2$, the efficiency of extraction becomes poor, because the solubility of lipids is significantly decreased. To the contrary, at pressures higher than 500 kg/cm$^2$, extraction is not economical, because a greater apparatus cost is required, although the solubility of lipids is increased. At temperatures lower than 25° C., the efficiency of extraction becomes poor, as in the case at lower pressures. To the contrary, at temperatures higher than 80° C., some problems of quality are caused by denaturation of the lipoprotein and deterioration of its functional properties.

The purpose of the step of separating the extracted lipids from the sub- or supercritical fluid can readily be attained by changing the pressure and temperature of the fluid to the ranges of from 1 to 200 kg/cm$^2$, preferably from 1 to 100 kg/cm$^2$, and from 10° to 100° C., preferably from 30° to 80° C., respectively, thereby reducing the solubility of the lipids. Also, a stepwise change in the pressure and temperature makes it possible to fractionate the lipoprotein-containing substance having a reduced lipid content.

The purpose of the separation step can also be attained by introducing the sub- or supercritical fluid dissolving the lipids into a vessel filled with an adsorbent, while maintaining the same pressure and temperature conditions as those employed for extraction, and removing the lipids contained in the fluid by adsorption. Examples of the adsorbent to be used for this purpose are activated charcoal, activated clay, silica gel, activated alumina, magnesium silicate and β-cyclodextrin. Depending upon the kind of an adsorbent to be used, it is also possible to attain the selective removal by adsorption only of the particular lipid ingredients, such as cholesterol and fatty acids, among the lipids extracted from the lipoprotein-containing substance.

In the foregoing, the sub- or supercritical fluid after the separation of the extracted lipids therefrom may be used again in the extraction step, while controlling or maintaining the pressure and temperature conditions for extraction. In this case, the fluid is repeatedly used in the extraction and separation steps without going into the discard, which is advantageous from the economical point of view.

Further, the enzyme treatment step with proteolytic enzymes and/or lipolytic enzymes can be conducted beforehand or concurrently with the extraction step in which lipid extraction is conducted with a sub- or supercritical fluid.

Since the lipoprotein has a relatively stable structure in water as described above, the removal of lipids by extraction has an extremely low efficiency, even if it is only conducted with a sub- or supercritical fluid. Therefore, a change in the structure of the lipoprotein by proteolytic enzymes or lipolytic enzymes is essential for the efficient removal of lipids by extraction.

In the process of the present invention, it is not necessary to use a dried substance as a raw material, as in the case of a conventional process, and it is possible to handle the raw material as it is in a liquid state. For this reason, a further economical process can be realized by conducting the enzyme treatment with proteolytic enzymes and/or lipolytic enzymes in the form of an immobilized enzyme or by employing a continuous contact system in the removal of lipids by extraction with a sub- or supercritical fluid.

In case of such a continuous contact system, it is possible to be either the counter or parallel flow contact system. It is, however, necessary to make such a proper device that the efficient removal of lipids by extraction can be attained by, for example, charging an extraction column with packings to ensure a more proper contact time.

The lipoprotein-containing substances treated in the process of the present invention have reduced contents of neutral lipids and cholesterol at respective ratios of 30 to 90% in comparison with the starting raw material. These substances are used as a food material for preparing various kinds of food having reduced contents of neutral lipids and cholesterol. For example, they can be used for preparing various dishes such as scrambled eggs, egg soups, bacon and eggs, thick omelets, thin omelets, thick custard soups, coatings for fried food and the like. The prepared dishes have substantially the same flavor as that of the dishes prepared from conventional eggs. Moreover, they can be used, instead of conventional eggs, as a raw material for various food products such as mayonnaise, egg custard, bread, rare cake, sponge cake, doughnuts, puff pastry, cookies, fruit pie, soft pie, sugar-coating confectionary, custard, biscuits, crackers, castella, cream puffs, custard pudding, milk pudding, bavarois, mousse, ice cream, eggnog, noodles, pasta and the like. In these cases, almost no inferior flavor was found.

Further, they can be used as a raw material of dried egg sheets and "Kinshi-tamago" (strips of thin omelet) to be prepared with a drum.

The following Examples further illustrate the present invention in detail, but are not to be construed to limit the scope thereof.

EXAMPLE 1

To 300 g of liquid egg yolk, 60 mg of Lipase M (manufactured by Amano Seiyaku Co., Ltd.) was added, and allowed to react thereon with stirring at 40° C. for 2 hours. The decomposition ratio of triglycerides was 45%.

The liquid egg yolk thus treated was put into an extraction vessel of 1000 ml in volume, and carbon dioxide at a pressure of 230 kg/cm$^2$ and a temperature of 42° C. was introduced thereinto for 2 hours for extraction of lipids, which were then separated in a separation vessel of 500 ml in volume under the conditions of 1 kg/cm$^2$ and 40° C. As a result, 51 g of extracts was obtained. After this operation of removing lipids by extraction, 240 g of the liquid egg yolk was recovered from the extraction vessel.

The resulting liquid egg yolk had such an appearance that the tone of its color became slightly thin, and other characteristics thereof were the same as those of egg yolk used as the raw material. The removal ratios of lipids and cholesterol were 61% and 68%, respectively.

EXAMPLE 2

To 250 g of liquid egg yolk, 1.0 g of Protease A (manufactured by Amano Seiyaku Co., Ltd.) was added, and allowed to react thereon with stirring at 40° C. for 3 hours. The degree of solubilization in TCA was 6.8%.

The liquid egg yolk thus treated was put into an extraction vessel of 1000 ml in volume, and carbon dioxide at a pressure of 300 kg/cm$^2$ and a temperature of 45° C. was introduced thereinto for 2 hours for extraction of lipids, which were then separated in a separation vessel under the conditions of 50 kg/cm$^2$ and 45° C. As a result, 38 g of extracts was obtained. After this operation of removing lipids by extraction, 201 g of the liquid egg yolk was recovered from the extraction vessel.

The characteristics of the liquid egg yolk thus recovered were the same as those obtained in Example 1. The removal ratios of lipids and cholesterol were 55% and 59%, respectively.

EXAMPLE 3

To 350 g of liquid egg yolk, 35 mg of Lipase F (manufactured by Amano Seiyaku Co., Ltd.) and 100 mg of Protease A (manufactured by Amano Seiyaku Co., Ltd.) were added, and allowed to react thereon with stirring at 40° C. for 2 hours. The decomposition ratio of triglycerides and the degree of solubilization in TCA were 35% and 1.8%, respectively.

The liquid egg yolk thus treated was subjected to the removal of lipids by extraction under the same conditions as those employed in Example 2. As a result, 66 g of extracts was obtained and 273 g of the liquid egg yolk was recovered from the extraction vessel.

The characteristics of the liquid egg yolk thus recovered were the same as those obtained in Examples 1 and 2. The removal ratios of lipids and cholesterol were 71% and 77%, respectively.

EXAMPLE 4

To 300 g of liquid whole egg, 30 mg of lipase "Saiken" (manufactured by Yakuruto Honsha Co., Ltd.) was added, and allowed to react thereon with stirring at 45° C. for 5 hours. The decomposition ratio of triglycerides was 41%.

The liquid whole egg thus treated was put into an extraction vessel of 1000 ml in volume, and carbon dioxide at a pressure of 350 kg/cm$^2$ and a temperature of 38° C. was introduced thereinto for 4 hours for extraction of lipids, which were then separated in a separation vessel of 500 ml in volume under the conditions of 10 kg/cm$^2$ and 40° C. As a result, 21 g of extracts was obtained. After this operation of removing lipids by extraction, 271 g of the liquid whole egg was recovered from the extraction vessel.

The liquid whole egg thus recovered had an appearance remaining substantially unchanged in comparison with that found before the treatment. The removal ratios of lipids and cholesterol were 60% and 62%, respectively.

EXAMPLE 5

To 500 g of liquid egg yolk, 50 mg of Lipase M (manufactured by Amano Seiyaku Co., Ltd.) was added, and allowed to react thereon with stirring at 42° C. for 2 hours. The decomposition ratio of triglycerides was 28%.

The liquid egg yolk thus treated was fed at a rate of 5 g/min. to the top of an extraction column of 40 mm in inner diameter and 1800 mm in length, which had been charged with glass beads of 5 mm in diameter, and carbon dioxide at a pressure of 250 kg/cm$^2$ and a temperature of 45° C. was introduced at a flow rate of 400 N·l/min. into the column from its bottom for removal of lipids by extraction in a counter flow continuous contact system. The carbon dioxide from the column top was introduced into a separation vessel and the lipids contained therein were separated under the conditions of 1 kg/cm$^2$ and 35° C. As a result, 89 g of extracts was obtained and 392 g of the liquid egg yolk was recovered from the bottom of the extraction column.

The characteristics of the liquid egg yolk thus recovered had an appearance remaining substantially unchanged in comparison with those found before the treatment, similarly to the cases of Examples 1, 2, and 3. The removal ratios of lipids and cholesterol were 65% and 67%, respectively.

EXAMPLE 6

The removal of lipids by extraction was conducted in the same manner as that described in Example 5, except that 40 mg of Lipase M (manufactured by Amano Seiyaku Co., Ltd.) and 100 mg of Protease S (manufactured by Amano Seiyaku Co., Ltd.) were added to 500 g of liquid egg yolk, and allowed to react thereon with stirring at 42° C. for 2 hours. As a result, 387 g of the liquid egg yolk was recovered from the bottom of the extraction column, similarly to the case of Example 5. The removal ratio of lipids and cholesterol were 72% and 79%, respectively.

EXAMPLE 7

The enzyme treatment and removal of lipids by extraction were conducted in the same manner as that described in Example 5, except that 500 g of liquid whole egg was used as a raw material. As a result, 458 g of the liquid whole egg was recovered from the bottom of the extraction column. The removal ratios of lipids and cholesterol were 60% and 61%, respectively.

EXAMPLE 8

The enzyme treatment and removal of lipids by extraction were conducted in the same manner as that described in Example 5, except that 500 g of sugared egg yolk (obtained by addition of sucrose at a ratio of 20% to liquid egg yolk) was used as a raw material. As a result, 413 g of the sugared egg yolk was recovered from the bottom of the extraction column. The removal ratio of lipids and cholesterol were 70% and 74%, respectively.

EXAMPLE 9

To 300 g of liquid egg yolk, 100 units (25 µl) of Phospholipase C (derived from *Bacillus cereus*; manufactured by Boehringer Mannheim GmbH) were added, and allowed to react thereon with stirring at 40° C. for 3 hours. The decomposition ratio of phospholipids was 30%.

The liquid egg yolk thus treated was put into an extraction vessel of 1000 ml in volume, and carbon dioxide at a pressure of 250 kg/cm$^2$ and a temperature of 42° C. was introduced thereinto for 3 hours for extraction of lipids, which were then separated in a separation vessel of 500 ml in volume under the conditions of 50 kg/cm$^2$ and 38° C. As a result, 53 g of extracts was obtained. After this operation of removing lipids by extraction, 238 g of the liquid egg yolk was recovered from the extraction vessel. The removal ratio of lipids and cholesterol were 62% and 66%, respectively.

EXAMPLE 10

The enzyme treatment was applied to egg yolk and the removal of lipids by extraction was conducted in the same manner as that described in Example 1, except that carbon dioxide containing 3 wt % ethanol was used as an extraction solvent. The removal ratios of lipids and cholesterol were 88% and 86%, respectively.

EXAMPLE 11

To 1 kg of porcine blood plasma, 0.4 mg of Lipoprotein Lipase (manufactured by Toyobo Co., Ltd.) was added, and allowed to react thereon with stirring at 45° C. for 3 hours. The decomposition ratio of triglycerides was 42%. The porcine blood plasma thus treated was fed at a rate of 4 g/min. to the top of an extraction column of 40 mm in inner diameter and 1800 mm in length, which had been charged with Raschig rings (5 mm in outer diameter and 5 mm in height), and carbon dioxide at a pressure of 350 kg/cm$^2$ and a temperature of 42° C. was introduced at a flow rate of 500 N·l/min. into the column from its bottom for removal of lipids by extraction in a counter flow continuous contact system. The carbon dioxide from the top of the column was introduced into a separation vessel, and the lipids contained therein were separated under the conditions of 55 kg/cm$^2$ and 40° C. As a result, 1.6 g of extracts was obtained, and 990 g of the porcine blood plasma was recovered from the bottom of the extraction column.

The total lipid content was 150 mg per 100 g of the porcine blood plasma thus recovered, and the removal ratio of total lipids was 56%. The porcine blood plasma thus recovered had almost no beastly odor in comparison with that found before the treatment.

COMPARATIVE EXAMPLE 1

Without conducting enzyme treatment, 300 g of liquid egg yolk which was the same as that used in Example 1 was put into an extraction vessel of 1000 ml in volume, and the extraction was conducted with carbon dioxide under the same conditions as those employed in Example 1.

As a result, almost nothing was obtained as an extract, and it was, therefore, impossible to attain the removal of lipids containing cholesterol by extraction.

COMPARATIVE EXAMPLE 2

Without conducting enzyme treatment, 1 kg of porcine blood plasma which was the same as that used in Example 11 was subjected to the removal of lipids by extraction under the same conditions as those employed in Example 11.

As a result, no extract was obtained and the porcine blood plasma which was recovered from the bottom of the extraction column remained having a strong beastly odor.

EXAMPLE 12

To 300 g of liquid egg yolk which had been subjected to the enzyme treatment in the same manner as that described in Example 1, 100 g of medium-chain fatty acid triglycerides (manufactured by Nisshin Oil Mills Ltd.; ODO) was added, followed by mixing. The mixture was put into a vessel of 1000 ml in volume, and carbon dioxide at a pressure of 230 kg/cm$^2$ and a temperature of 45° C. was introduced thereinto for 1 hour for extraction of lipids, which were then separated under the conditions of 50 kg/cm$^2$ and 30° C. As a result, 102 g of extracts was obtained. Although the lipid content in the liquid egg yolk after this treatment exhibited almost no change in comparison with that before the treatment, it was found that 66% of cholesterol was removed.

EXAMPLE 13

Three hundred grams of liquid egg yolk which had been subjected to the enzyme treatment in the same manner as that described in Example 1 were put into an extraction vessel of 1000 ml in volume, and carbon dioxide at a pressure of 250 kg/cm$^2$ and a temperature of 45° C. was introduced thereinto for extraction of lipids. The carbon dioxide after the extraction was allowed to pass through an adsorption vessel of 500 ml in volume, which had been connected next to the extraction vessel and filled with 100 g of activated clay, under the same pressure and temperature conditions as those described above. Thereafter, the removal of lipids by adsorption on the activated clay was conducted in a circulating system where the carbon dioxide was repeatedly allowed to pass through the extraction vessel and then through the adsorption vessel for 2 hours, while maintaining the same pressure and temperature conditions as those described above. As a result of this treatment, the removal ratios of lipids and cholesterol in the liquid egg yolk were 19% and 71%, respectively.

EXAMPLE 14

Under the same conditions as those described in Example 1, about 10 kg of egg yolk was treated to prepare about 8 kg of liquid egg yolk having reduced contents of cholesterol and neutral lipids. The analytical data of egg yolk as the raw material and the treated liquid egg yolk of this example are shown in Table 1.

For the treated liquid egg yolk of this example, the removal ratios of cholesterol, lipids and neutral lipids were about 69%, about 55% and 80%, respectively, and the remaining ratio of phospholipids was 100%. To the treated liquid egg yolk of this example, water was added at a ratio of 20%, resulting in a liquid egg yolk (hereinafter referred to as prepared liquid egg yolk), which was used in the subsequent test.

TABLE 1

| Items | Egg yolk as raw material | Treated liquid egg yolk |
|---|---|---|
| Water (wt %) | 52.0 | 61.3 |
| Proteins (wt %) | 15.0 | 18.8 |
| Lipids (wt %) | | |
| Neutral lipids | 20.3 | 5.1 |
| Phospholipids | 9.5 | 11.9 |
| Carbohydrate (wt %) | 0.5 | 0.6 |
| Ash (wt %) | 1.4 | 1.8 |
| Cholesterol (wt %) | 1.3 | 0.5 |

According to a conventional method, comparison between the egg yolk as the raw material and the prepared liquid egg yolk was made with respect to the capacity, activity, and stability of emulsification, and no difference was found therebetween.

The following food was prepared by using the prepared liquid egg yolk thus obtained.

OMELET

The prepared liquid egg yolk (200 g) was taken in a bowl, to which liquid egg white (550 g) and some amounts of sugar and salt were added, and the mixture was well mixed with a beater. The mixture was baked on a frying pan with a small amount of salad oil to prepare an omelet (omelet A). Likewise, according to the same manner, an omelet (omelet B) was prepared, except that conventional eggs were used instead of the prepared liquid egg yolk. The organolepic evaluation was conducted by 20 panelists. The results are shown in Table 2. The figures in Table 2 are the number of panelists that agreed to the evaluation.

TABLE 2

| Evaluation | Omelet A | Omelet B |
|---|---|---|
| Better flavor | 13 | 7 |
| Better taste | 11 | 9 |
| Better body | 5 | 15 |
| Better chewing | 8 | 12 |
| Better overall evaluation | 12 | 8 |

As seen from Table 2, although omelet A had a pale yellow color in comparison with omelet B, the overall evaluation from the organolepic results was good. The cholesterol content, lipid content and caloric value of omelet A were reduced to about 31%, about 45% and about 68% of the corresponding one of omelet B, respectively.

SPONGE CAKE

A mixture of egg white (500 g) and sugar (420 g) was well frothed in bowl A by agitating with a beater. Separately, a mixture of the prepared liquid egg yolk (700 g), sugar (400 g), and water (150 g) was well frothed in bowl B by agitating with a beater.

The contents of bowl B was put into bowl A, after which the mixture was well mixed and low gluten wheat flour (800 g) was added thereto, followed by slight mixing.

A small amount of vanilla essence was added thereto, and the mixture was baked in an oven to prepare a sponge cake (sponge cake A). Likewise, according to the same manner, a sponge cake (sponge cake B) was prepared, except that conventional liquid egg yolk was used instead of the prepared liquid egg yolk. The organolepic evaluation was conducted by 20 panelists. The results are shown in Table 3. The figures in Table 3 are the number of panelists that agreed to the evaluation.

TABLE 3

| Evaluation | Sponge cake A | Sponge cake B |
|---|---|---|
| Better flavor | 14 | 6 |
| Better taste | 13 | 7 |
| Better body | 7 | 13 |
| Better chewing | 10 | 10 |
| Better overall evaluation | 13 | 7 |

The cholesterol content and lipid content in sponge cake A were reduced to about 31% and about 50% of the corresponding one of sponge cake B, respectively.

CUSTARD PUDDING

A mixture of whole egg (200 g), the prepared liquid egg yolk (240 g), and sugar (360 g) was well stirred in a bowl, after which milk (1.2 kg) was added thereto with preventing bubbling. Further, vanilla essence (1 g) and a small amount of rum were added thereto, and the mixture was dispensed as appropriate portions into 300 ml cups. These cups were heated with steam in an oven at 150° to 160° C. for 40 minutes, followed by cooling, to prepare a custard pudding (pudding A).

Likewise, according to the same manner, a custard pudding (pudding B) was prepared, except that conventional liquid egg yolk was used instead of the prepared liquid egg yolk. The organolepic evaluation was conducted by 20 panelists. The results are shown in Table 4. The figures in Table 4 are the number of panelists that agreed to the evaluation.

TABLE 4

| Evaluation | Custard pudding A | Custard pudding B |
|---|---|---|
| Better flavor | 13 | 7 |
| Better taste | 12 | 8 |
| Better body | 9 | 11 |
| Better chewing | 9 | 11 |
| Better overall evaluation | 11 | 9 |

The cholesterol content and neutral lipid content in custard pudding A were reduced to about 48.3% and about 56.8% of the corresponding one of custard pudding B, respectively.

MAYONNAISE

According to the formulation as shown in Table 5, the prepared liquid egg yolk, sugar, salt, powdered mustard, pepper, paprika, and one half of vinegar were mixed in a stainless steel pot to form a uniform mixture which was then put into a mixer. The mixture was agitated by a mixer with addition of salad oil and the remaining half of vinegar thereto, resulting in an emulsified mixture. Further, the contents of the mixer were put into a stainless steel vessel, and treated with a colloid mill for several seconds to prepare a mayonnaise (mayonnaise A).

Likewise, according to the same manner, a mayonnaise (mayonnaise B) was prepared, except that conventional egg yolk was used instead of the prepared liquid egg yolk. The formulation of mayonnaise B is also shown in Table 5. The organolepic evaluation was conducted by 20 panelists. The results are shown in Table 6. The figures in Table 6 are the number of panelists that agreed to the evaluation.

TABLE 5

| | Mayonnaise | |
|---|---|---|
| Ingredients | A (wt %) | B (wt %) |
| Conventional egg yolk | — | 18.0 |
| Treated liquid egg yolk | 18.0 | — |
| Vinegar | 9.4 | 9.4 |
| Sugar | 2.2 | 2.2 |
| Salt | 1.3 | 1.3 |
| Powdered mustard | 0.9 | 0.9 |
| Pepper | 0.1 | 0.1 |
| Paprika | 0.1 | 0.1 |
| Salad oil | 68.0 | 68.0 |

TABLE 6

| Items | Mayonnaise A | Mayonnaise B |
|---|---|---|
| Better flavor | 15 | 5 |
| Better taste | 13 | 7 |
| Better body | 8 | 12 |
| Better smoothness | 11 | 9 |
| Better overall evaluation | 10 | 10 |

As shown in Table 6, no difference in overall evaluation was found between mayonnaise A and B. When both mayonnaise A and mayonnaise B were allowed to stand at 50° C. for 10 and 20 days, no difference in appearance was found between mayonnaise A and B. The cholesterol content in mayonnaise A was about 31% of that of mayonnaise B.

What is claimed is:

1. A process for producing a liquid egg yolk having a reduced lipid content, which comprises the steps of: treating a liquid egg yolk with at least one enzyme selected from the group consisting of proteolytic enzymes and lipolytic enzymes so that when said at least one proteolytic enzyme is used the degree of solubilization in 0.22M trichloroacetic acid of proteins in the liquid egg yolk after the treatment with the proteolytic enzyme is from 1.5% to 30% or when said at least one lipolytic enzyme is used the decomposition ratio of lipids in the liquid egg yolk after the treatment with the lipolytic enzyme is from 5% to 50%; bringing the enzyme treated liquid egg yolk into contact with a sub- or supercritical fluid to extract lipid therefrom sufficient to form a reduced lipid liquid egg yolk; and separating the extracted lipid from the enzyme treated liquid egg yolk.

2. A process according to claim 1, wherein the lipolytic enzymes are at least one selected from the group consisting of lipases, lipoprotein lipases and phospholipases.

3. A process according to claim 2, wherein the decomposition ratio of lipids in the liquid egg yolk after the treatment with lipases or lipoprotein lipases is from to 80%.

4. A process according to claim 2, wherein the decomposition ratio of lipids in the liquid egg yolk after the treatment with phospholipases is from 1% to 80%.

5. A process according to claim 1, wherein the extraction of lipids is conducted with a mixture of the sub- or supercritical fluid and a co-solvent.

6. A process according to claim 5, wherein the co-solvent is at least one selected from the group consisting of ethanol, methanol, acetone, hexane, palm kernel oil, coconut oil and medium-chain fatty acid triglycerides.

7. A process according to claim 1 or 5, wherein the lipid is at least one selected from the group consisting of monoglycerides, diglycerides, triglycerides, fatty acids, cholesterol and phospholipids.

8. A process according to claim 1, wherein the liquid egg yolk treated with the enzyme is mixed with a co-solvent, after which the lipid is extracted with the sub- or supercritical fluid.

9. A process according to claim 8, wherein the co-solvent is at least one selected from the group consisting of palm kernel oil, coconut oil and medium-chain fatty acid triglycerides.

10. A process according to claim 8, wherein the lipid is cholesterol or a fatty acid.

11. A process according to claim 1, 5 or 8, wherein the extraction of lipids is conducted at a pressure of from 50 to 500 kg/cm$^2$ and a temperature of from 25° to 80° C.

12. A process according to claim 1, 5 or 8, wherein the liquid egg yolk treated with the enzyme is brought into contact with the sub- or supercritical fluid in a counter or parallel flow continuous contact system for extraction of lipids.

13. A process according to claim 1, 5 or 8, wherein the lipid extracted from the liquid egg yolk is separated from the sub- or supercritical fluid at a pressure of from 1 to 200 kg/cm$^2$ and a temperature of from 10° to 100° C.

14. A process according to claim 1, 5 or 8, wherein the lipid extracted from the liquid egg yolk is separated from the sub- or supercritical fluid by adsorbing the lipid on an adsorbent.

15. A process according to claim 14, wherein the adsorbent is selected from the group consisting of activated charcoal, activated clay, silica gel, activated alumina, magnesium silicate and β-cyclodextrin.

16. A process according to any one of claims 1, 5, or 8, wherein the sub- or supercritical fluid is carbon dioxide.

17. A process according to claim 12, wherein the sub- or supercritical fluid is carbon dioxide.

18. A process according to claim 13, wherein the sub- or supercritical fluid is carbon dioxide.

19. A process according to claim 14, wherein the sub- or supercritical fluid is carbon dioxide.

* * * * *